US012566131B2

(12) United States Patent
Ceglinski et al.

(10) Patent No.: US 12,566,131 B2
(45) Date of Patent: Mar. 3, 2026

(54) METHODS FOR PRODUCING SEED CORN FOR USE IN GROWING CORN PLANTS, USING COMBINE HARVESTERS

(71) Applicant: MONSANTO TECHNOLOGY LLC, Saint Louis, MO (US)

(72) Inventors: Jarrett Ryan Ceglinski, Damiansville, IL (US); Jack Glenn Fombelle, Monticello, IL (US); David Everett Johnson, Esmond, IL (US); Jason W. Knoche, Mililani, HI (US); Adam Harold Leek, O'Fallon, MO (US); Kevin M. Mcalister, Wentzville, MO (US); Kirk Murlin Remund, St. Charles, MO (US); Steven John Swanton, Wentzville, MO (US); Dustin Mitchell Theis, O'Fallon, IL (US)

(73) Assignee: MONSANTO TECHNOLOGY LLC, Saint Louis, MO (US)

( * ) Notice: Subject to any disclaimer, the term of this patent is extended or adjusted under 35 U.S.C. 154(b) by 0 days.

(21) Appl. No.: 18/649,931

(22) Filed: Apr. 29, 2024

(65) Prior Publication Data

US 2024/0276915 A1 Aug. 22, 2024

Related U.S. Application Data

(62) Division of application No. 17/110,201, filed on Dec. 2, 2020, now Pat. No. 11,968,925.

(Continued)

(51) Int. Cl.
*G01N 21/3554* (2014.01)
*A01D 41/127* (2006.01)
(Continued)

(52) U.S. Cl.
CPC ..... *G01N 21/3554* (2013.01); *A01D 41/1277* (2013.01); *A01D 91/04* (2013.01);
(Continued)

(58) Field of Classification Search
CPC ... G01N 2201/0646; G01N 2021/8466; G01N 33/025; G01N 27/048; G01N 21/84;
(Continued)

(56) References Cited

U.S. PATENT DOCUMENTS 4,954,783 A 9/1990 Spry
5,343,761 A * 9/1994 Myers ..................... G01F 1/206
73/861.73
(Continued)

FOREIGN PATENT DOCUMENTS

CN 102067771 A 5/2011
CN 204132018 U 2/2015
(Continued)

OTHER PUBLICATIONS

Laurenzi Tom: "What's the Ideal Moisture Content for Grain?", Feb. 20, 2018 (Feb. 20, 2018), pp. 1-5.

*Primary Examiner* — Arpad Fabian-Kovacs
(74) *Attorney, Agent, or Firm* — Harness, Dickey & Pierce, P.L.C.

(57) ABSTRACT

Combine harvesters are provided for use in harvesting seed corn from corn plants in fields. In connection therewith, a method for producing such seed corn from the corn plants, for use in growing subsequent corn plants, includes measuring a moisture content of corn kernels on ears of the corn plants in the field and removing, by one of the combine harvesters, the ears of corn from the corn plants when the moisture content satisfies a threshold moisture content. The method then includes separating the corn kernels from cobs of the ears of corn onboard the combine harvester and (Continued)

collecting the separated corn kernels for use as seed corn, whereby one or more subsequent corn plants can be grown from the collected corn kernels.

21 Claims, 9 Drawing Sheets

Related U.S. Application Data

(60) Provisional application No. 62/943,681, filed on Dec. 4, 2019.

(51) Int. Cl.

| | |
|---|---|
| *A01D 91/04* | (2006.01) |
| *A01F 11/06* | (2006.01) |
| *A01F 12/24* | (2006.01) |
| *A01F 12/44* | (2006.01) |
| *B07C 5/00* | (2006.01) |
| *F26B 3/00* | (2006.01) |
| *G01J 3/02* | (2006.01) |
| *G01N 21/359* | (2014.01) |
| *G01N 27/04* | (2006.01) |
| *G01N 33/02* | (2006.01) |
| *A01D 45/02* | (2006.01) |
| *A01F 12/10* | (2006.01) |
| *A01F 25/22* | (2006.01) |
| *G01F 1/66* | (2022.01) |
| *G01N 21/84* | (2006.01) |
| *G06F 3/0481* | (2022.01) |
| *G06F 3/04886* | (2022.01) |

(52) U.S. Cl.
CPC .............. *A01F 11/06* (2013.01); *A01F 12/24* (2013.01); *A01F 12/446* (2013.01); *B07C 5/00* (2013.01); *F26B 3/00* (2013.01); *G01J 3/0272* (2013.01); *G01N 21/359* (2013.01); *G01N 27/048* (2013.01); *G01N 33/025* (2013.01); *A01D 45/025* (2013.01); *A01F 12/10* (2013.01); *A01F 12/444* (2013.01); *A01F 25/22* (2013.01); *G01F 1/666* (2013.01); *G01N 21/84* (2013.01); *G01N 2021/8466* (2013.01); *G01N 2201/0646* (2013.01); *G06F 3/0481* (2013.01); *G06F 3/04886* (2013.01)

(58) Field of Classification Search
CPC . G01N 21/359; G01N 21/3554; G01J 3/0272; F26B 3/00; B07C 5/00; A01F 25/22; A01F 12/444; A01F 12/44; A01F 12/26; A01F 12/24; A01F 12/10; A01F 11/06; A01D 91/04; A01D 61/008; A01D 45/025; A01D 45/021; A01D 41/1277; A01D 41/127; A01D 41/1208; G01F 1/666; G06F 3/04886; G06F 3/0481
See application file for complete search history.

(56) References Cited

U.S. PATENT DOCUMENTS

| | | | | |
|---|---|---|---|---|
| 6,421,990 | B1 | 7/2002 | Ohlemeyer et al. | |
| 6,747,461 | B2 * | 6/2004 | Corak | F26B 25/22 |
| | | | | 73/73 |
| 9,278,377 | B2 * | 3/2016 | Brumback | B07C 5/00 |
| 10,019,791 | B2 | 7/2018 | Young et al. | |
| 10,034,423 | B2 * | 7/2018 | Dybro | A01D 41/127 |
| 10,713,768 | B2 | 7/2020 | Berghoefer et al. | |
| 10,937,148 | B2 | 3/2021 | Mello | |
| 11,191,215 | B1 * | 12/2021 | Robertson | A01D 41/1276 |
| 11,474,523 | B2 * | 10/2022 | Vandike | A01D 41/127 |
| 11,727,680 | B2 * | 8/2023 | Vandike | G06V 20/56 |
| | | | | 382/100 |
| 11,825,768 | B2 * | 11/2023 | Vandike | A01D 41/141 |
| 12,022,772 | B2 * | 7/2024 | Yanke | A01D 41/127 |
| 12,127,500 | B2 * | 10/2024 | Palla | G05D 1/0278 |
| 2004/0103456 | A1 * | 5/2004 | Margaret | C12N 15/8261 |
| | | | | 800/278 |
| 2004/0205846 | A1 * | 10/2004 | Chye | C07K 14/811 |
| | | | | 435/468 |
| 2008/0171269 | A1 | 7/2008 | Dunn | |
| 2009/0137295 | A1 | 5/2009 | Redekop et al. | |
| 2010/0148048 | A1 | 6/2010 | Abbas et al. | |
| 2012/0110954 | A1 | 5/2012 | Brumback et al. | |
| 2014/0083073 | A1 | 3/2014 | Doerscher, Sr. | |
| 2016/0000008 | A1 * | 1/2016 | Schøler | A01D 41/1272 |
| | | | | 56/10.2 R |
| 2016/0003656 | A1 * | 1/2016 | Gelinske | G01N 33/0098 |
| | | | | 73/861.18 |
| 2016/0078611 | A1 * | 3/2016 | Butts | G01S 13/867 |
| | | | | 382/110 |
| 2016/0300363 | A1 | 10/2016 | Young et al. | |
| 2017/0188512 | A1 | 7/2017 | Fromm | |
| 2017/0235471 | A1 * | 8/2017 | Schøler | G01F 1/666 |
| | | | | 715/772 |
| 2018/0000011 | A1 * | 1/2018 | Schleusner | G01S 13/87 |
| 2022/0138868 | A1 * | 5/2022 | Jarugumilli | G06F 17/10 |
| | | | | 705/7.23 |

FOREIGN PATENT DOCUMENTS

| | | | | |
|---|---|---|---|---|
| CN | 204948768 | U | 1/2016 | |
| CN | 106091631 | A | 11/2016 | |
| CN | 106659125 | A | 5/2017 | |
| CN | 110199665 | A | 9/2019 | |
| CN | 212629231 | U | 3/2021 | |
| CN | 113049530 | A | 6/2021 | |
| DE | 102015226349 | A1 | 6/2017 | |
| DE | 102013100057 | B4 * | 10/2021 | A01F 12/26 |
| EP | 1493318 | B1 * | 9/2016 | A01D 41/127 |
| EP | 4026419 | A1 | 7/2022 | |
| JP | H09275767 | A | 10/1997 | |
| KR | 200244219 | Y1 | 10/2001 | |
| KR | 100934410 | B1 | 12/2009 | |
| WO | WO-0189288 | A1 | 11/2001 | |
| WO | WO-0248687 | A2 | 6/2002 | |
| WO | WO-2014050524 | A1 | 4/2014 | |
| WO | WO-2016040959 | A1 * | 3/2016 | A01D 41/1271 |
| WO | WO-2016145334 | A1 | 9/2016 | |
| WO | WO-2017021285 | A1 | 2/2017 | |
| WO | WO-2018236787 | A1 | 12/2018 | |

* cited by examiner

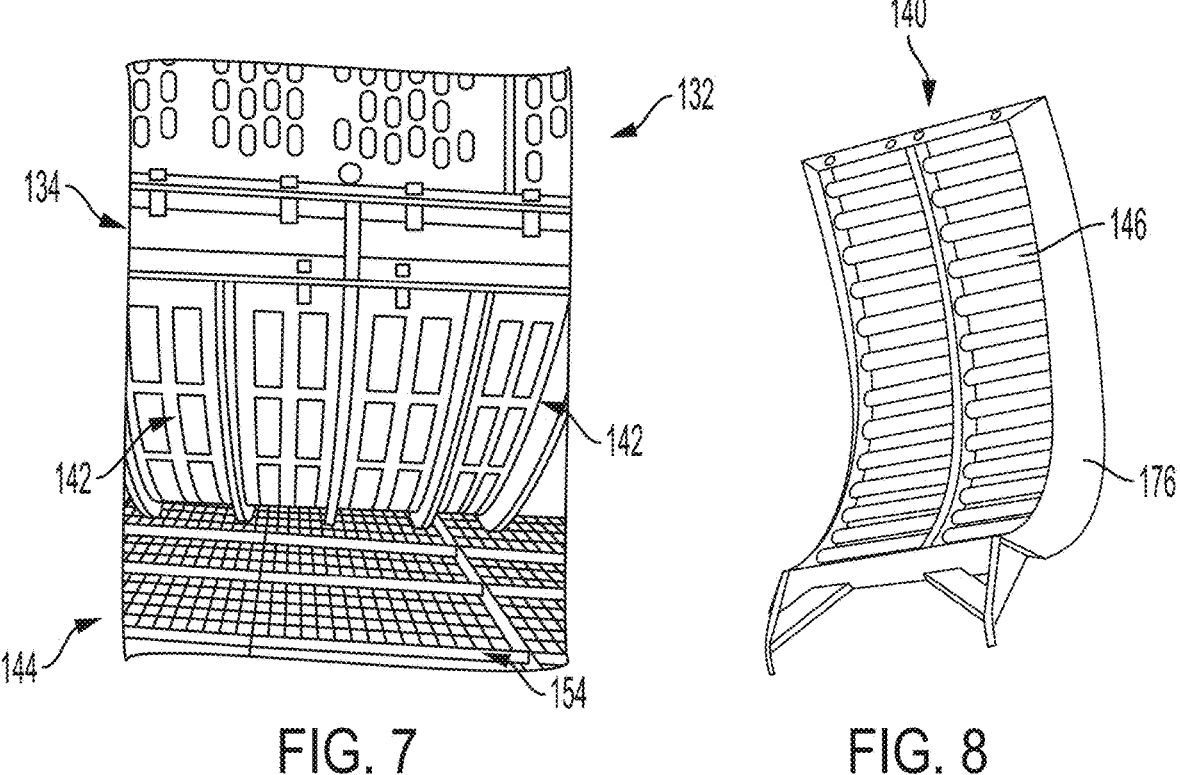
FIG. 7
FIG. 8
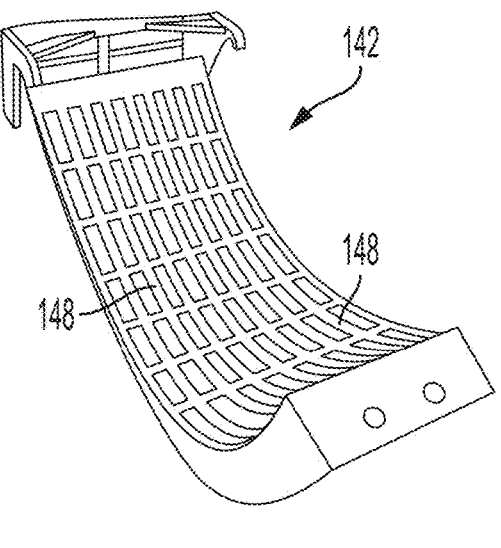
FIG. 9

METHODS FOR PRODUCING SEED CORN FOR USE IN GROWING CORN PLANTS, USING COMBINE HARVESTERS

CROSS-REFERENCE TO RELATED APPLICATIONS

This application is a divisional of U.S. patent application Ser. No. 17/110,201, filed Dec. 2, 2020, which claims the benefit of, and priority to, U.S. Provisional Application No. 62/943,681, filed on Dec. 4, 2019. The entire disclosure of each of the above-referenced applications is incorporated herein by reference.

FIELD

The present disclosure generally relates to agricultural harvesting machines and, in particular, to combine harvesters for use in harvesting corn (e.g., seed corn, etc.) and related methods of using such combine harvesters (e.g., to produce seed corn, bulk up populations of seed corn, etc.).

BACKGROUND

This section provides background information related to the present disclosure which is not necessarily prior art.

Corn plants are known to be grown in fields for commercial purposes, for example, for use as seed (to grow subsequent corn plants), or for use as feed (for animals), etc. At a point in the growing cycle, the corn plants are harvested or picked, whereby ears of corn plants are broken off from stocks of the corn plants and collected. Kernels of corn are then removed from cobs of the ears of corn and collected for subsequent use (e.g., as seed, as feed, etc.). In connection therewith, mechanized machines for harvesting the corn plants from the fields are known to include corn ear pickers, which remove the ears of corn from the corn plants and collect the ears intact within the pickers. The collected ears of corn are then transported to processing facilitates, still intact to help protect the kernels during transport and inhibit undesired loss of kernels, whereat the ears of corn are de-husked and dried and the kernels are then removed from the cobs.

SUMMARY

This section provides a general summary of the disclosure, and is not a comprehensive disclosure of its full scope or all of its features.

Example embodiments of the present disclosure generally relate to combine harvesters for use in harvesting corn plants from a field, based on identification of one or more characteristics of the corn plants. In one example embodiment, such a combine harvester generally includes a corn header configured to engage corn plants in a field having the one or more characteristics and separate cars of corn from the corn plants, as the combine harvester moves through the field, and a threshing unit configured to receive the cars of corn from the corn header and remove corn kernels from the cars of corn on board the combine harvester. The threshing unit generally includes a housing having multiple concaves and multiple separating grates disposed along a length of the housing and a rotor disposed within the housing and configured to rotate relative to the housing, wherein a spacing between the rotor and the housing is between about 0.4 inches and about 1.5 inches along a length of the rotor. The combine harvester of this example embodiment also includes a feeder unit disposed generally between the corn header and the threshing unit, where the feeder unit is configured to receive the cars of corn from the corn header and move the received cars of corn to the threshing unit, a separating unit disposed generally below the threshing unit and configured to receive the corn kernels removed from the cars of corn, through the multiple concaves and the multiple separating grates, and a hopper configured to receive the corn kernels from the separating unit and store the corn kernels onboard the combine harvester.

Example embodiments of the present disclosure also generally relate to methods for producing seed corn for use in growing corn plants. In one example embodiment, such a method generally includes measuring a moisture content of corn kernels on cars of corn plants in a field; removing, by a combine harvester, the cars of corn from the corn plants in the field, when the moisture content satisfies a threshold moisture content; separating the corn kernels from cobs of the cars of corn onboard the combine harvester while in the field; and collecting the separated corn kernels for use as seed corn, whereby one or more corn plants can be grown from the corn kernels collected by the combine harvester.

In another example embodiment, a method for producing seed corn for use in growing corn plants generally includes determining that corn plants in a field include one or more desired characteristics; directing a combine harvester to the field based on the determination, when a moisture content of corn kernels on ears of the corn plants satisfy a threshold moisture content; removing, by the combine harvester, the ears of corn from the corn plants; separating the corn kernels from cobs of the ears of corn onboard the combine harvester; and collecting the separated corn kernels for use as seed corn, whereby one or more corn plants can be grown from the collected corn kernels.

In a further example embodiment, a method for producing seed corn for use in growing corn plants generally includes removing, by a combine harvester, ears of corn from corn plants in a field; separating the corn kernels from cobs of the ears of corn onboard the combine harvester while in the field; and collecting, by the combine harvester, a supply of the separated corn kernels for use as seed corn; wherein cold germination of the collected supply of corn kernels is at least about 75%; and wherein warm germination of the collected supply of corn kernels is at least about 75%.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is an enlarged, fragmentary perspective view of multiple concaves of the housing of the threshing unit of the combine harvester;

FIG. 8 is a perspective view of the multiple concaves of FIG. 7;

FIG. 9 is a perspective view of another separating grate that may be included in the housing of the threshing unit of the combine harvester;

Corresponding reference numerals indicate corresponding parts throughout the several views of the drawings.

DETAILED DESCRIPTION

Figure 1:
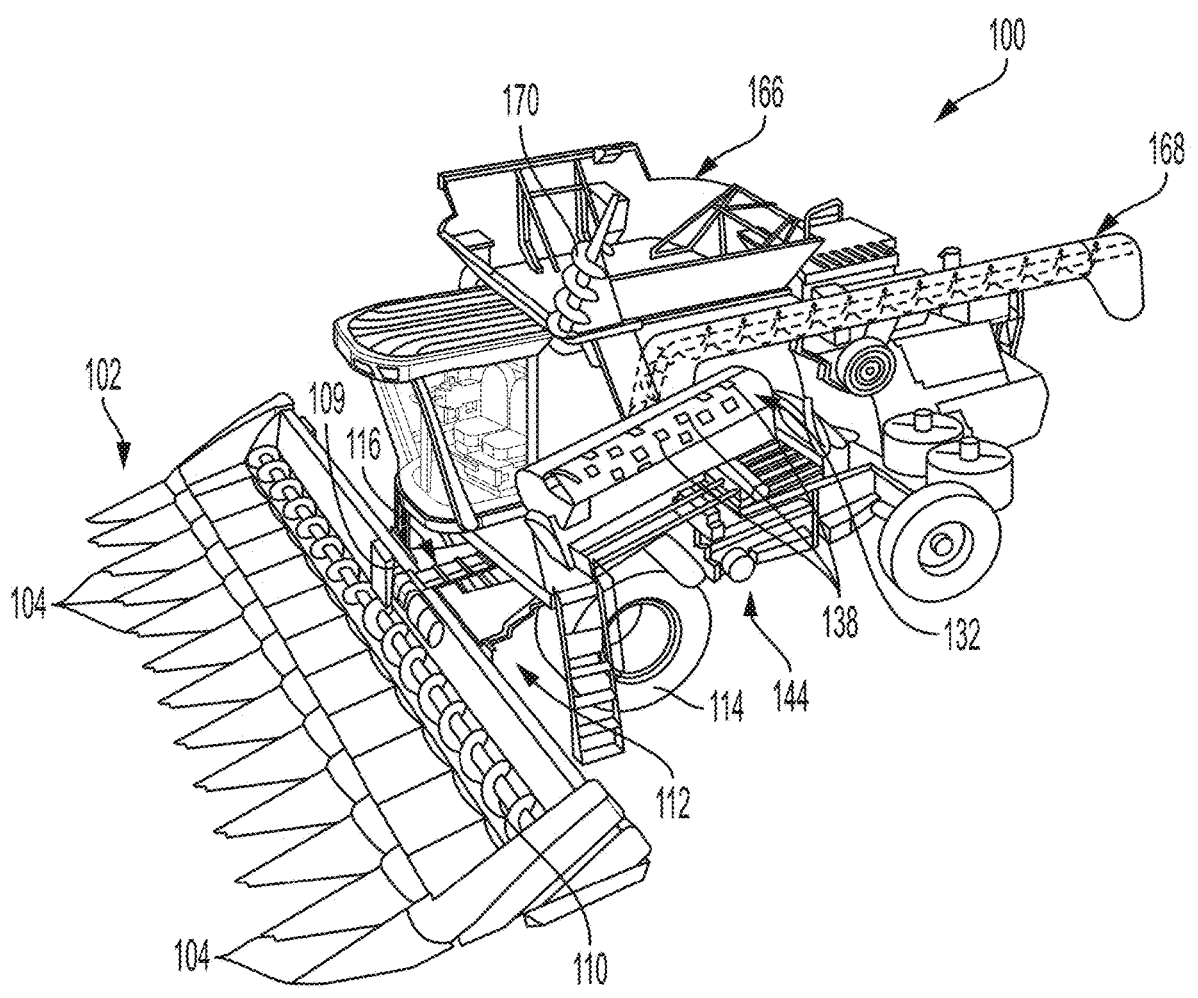
FIG. 1 is a perspective view of an example combine harvester modified to include one or more aspects of the present disclosure for use in harvesting seed corn.

Conventionally, in the context of seed corn production, corn plants are harvested from fields using mechanized ear pickers. In so doing, ears of corn are picked from corn plants in the fields and transported, intact, to processing facilities where husks are removed from the ears of corn, and the ears of corn are then dried and shelled (thereby removing kernels (broadly, seed corn) from cobs of the ears of corn). In this process, the ears of corn are initially picked from the corn plants in the field when the kernels of corn have average moisture contents of between about 32% and about 38% (e.g., based on a sampling of corn plants in the field, etc.), which helps maintain the corn kernels on cobs of the ears of corn as they are picked and which allows for harvesting the corn plants as soon as possible (e.g., to avoid potential damage to the corn plants by leaving them in the field any longer than necessary, etc.). The picked ears of corn are then dried, in dryers, at temperatures of about 95 degrees Fahrenheit (° F.) until the kernels have average moisture contents of about 12%. This conventional process, though, can take upwards of 80 hours or more to complete, from the time the cars of corn are picked and dried to the time the kernels are removed from the cars and stored as bulk dry shell seed corn (which may then be used to grow, for example, corn plants that produce No. 2 yellow corn (and which may then be used as feed, for ethanol production, etc.), etc.). What's more, because the cars of corn (once picked) are transported and processed intact, the resources (e.g., pickers, transport corn trucks, de-huskers, dryers (and drying times), shellers, etc.) required to accommodate the extra corn material (husks, cobs, etc.) can be extensive.

As an alternative, corn plants (such as those that produce No. 2 yellow corn, etc.) may be harvested from fields using combine harvesters. In connection therewith, the corn plants are again conventionally harvested when the kernels of corn have average moisture contents of between about 32% and about 38% (e.g., based on a sampling of corn plants in the field, etc.), which allows for harvesting the corn plants as soon as possible (e.g., to avoid potential damage to the corn plants by leaving them in the field any longer than necessary, etc.). In doing so, though, the resulting corn kernels collected by the combine harvesters (e.g., No. 2 yellow corn kernels, etc.) have relatively low germination viability, for example, due to damage to the corn kernels during the harvesting process, etc.

Uniquely, the present disclosure generally relates (in one or more embodiments) to use of combine harvesters in seed corn production, to harvest corn plants from fields and produce bulk supplies of dry shell seed corn from the harvested corn plants. In connection therewith, the combine harvesters can facilitate production of the seed corn supplies in a shorter amount of time, and with less demand on resources, than the conventional corn ear pickers. In particular, by way of the present disclosure, corn plants in fields (e.g., designated for seed corn production, etc.) are harvested by the combine harvesters, whereby the cars of corn removed from the corn plants are de-husked and shelled onboard the combine harvesters. The kernels of corn are then removed from the combine harvesters to trucks (via dump carts, etc.) for transport to processing facilities, where the separated kernels are dried and stored (e.g., as supplies of seed corn, etc.). As can be appreciated, since the cars of corn are de-husked and shelled onboard the combine harvesters, the time used to subsequently de-husk and dry the intact cars of corn in the conventional ear picking process (e.g., again, which can be upwards of 80 hours or more, etc.) is not required in the present disclosure. What's more, fewer resources are required to subsequently process the separated kernels (as compared to the intact cars of corn provided from the corn ear pickers), not only in the elimination of the need for separate de-husking and shelling equipment but also in the need of fewer transport corn trucks, fewer corn driers (and shorter drying times, as will be described more hereinafter), etc.

Example embodiments will now be described more fully with reference to the accompanying drawings. The description and specific examples included herein are intended for purposes of illustration only and are not intended to limit the scope of the present disclosure.

FIG. 1 illustrates an example embodiment of a combine harvester 100 (broadly, an agricultural harvester) including one or more aspects of the present disclosure. As will be described, the combine harvester 100 is configured (e.g., is constructed and operable, etc.) to harvest whole cars of corn from corn plants in a field, as the combine harvester 100 moves through the field. The combine harvester 100 is then configured to remove kernels of corn (broadly, corn seeds) from the cars of corn, and to collect the kernels for subsequent processing, use, etc. (e.g., for subsequent use as seed corn, etc.). In particular herein, the collected kernels are collected to produce bulk supply of dry shell seed corn (broadly, seed corn) that may be used to grow subsequent corn plants (e.g., No. 2 yellow corn plants, etc. such that the collected seed corn serves as a predecessor to the No. 2 yellow corn plants).

Figure 2:
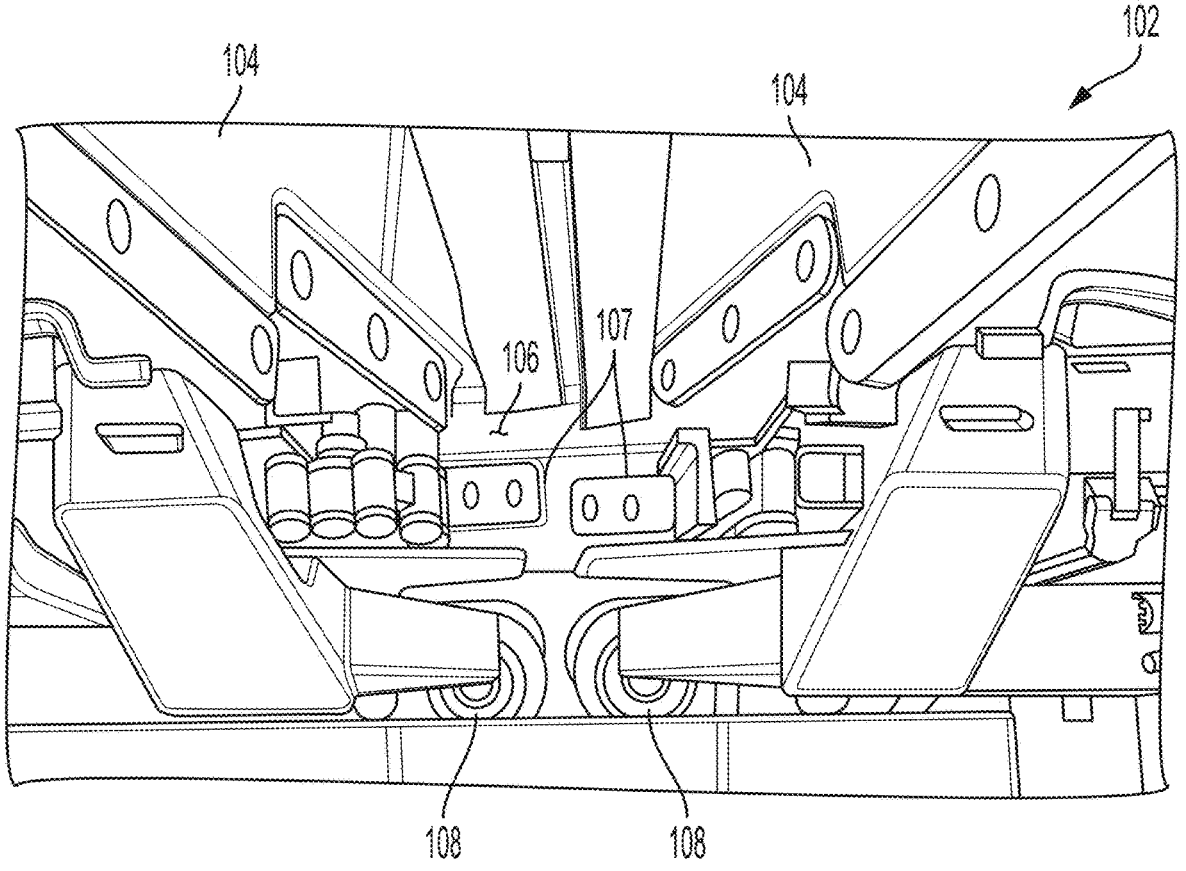
FIG. 2 is an enlarged, fragmentary perspective view of an example corn header that may be used with the combine harvester.

As shown in FIGS. 1 and 2, the illustrated combine harvester 100 includes a corn header 102 configured to receive (or collect) the cars of corn from the corn plants in the field, and to channel (or direct) the cars of corn to the combine harvester 100 where the kernels of corn are then removed from the cobs of the cars of corn. In connection therewith, the corn header 102 (as releasably coupled to a frame of the combine harvester 100) includes multiple row dividers 104 (or snouts) configured to direct rows of corn stalks (within the field) between adjacent ones of the row dividers 104 and into a corresponding separation chamber 106 (generally defined between the adjacent ones of the row dividers 104 (FIG. 2)). In so doing, paddles 107 and stalk rollers 108 (e.g., rounded cylinders with blades, etc.) located between the row dividers 104 (generally within the corresponding separation chambers 106) operate to snap the corn stalks and separate the cars of corn therefrom. The corn stalks then fall to the ground under the combine harvester 100. And, the removed cars of corn move through the respective separation chambers 106 to an auger 110, which in turn directs the cars of corn to a feeder unit 112 of the combine harvester 100 (via opening 109 in the header 102). With that said, in the illustrated embodiment, the stalk rollers 108 of the corn header 102 are configured to rotate at speeds of between about 1,000 rotations per minute (rpm) and about 1,200 rpm, to thereby facilitate removal of the cars of corn from the stalks.

Figure 3:
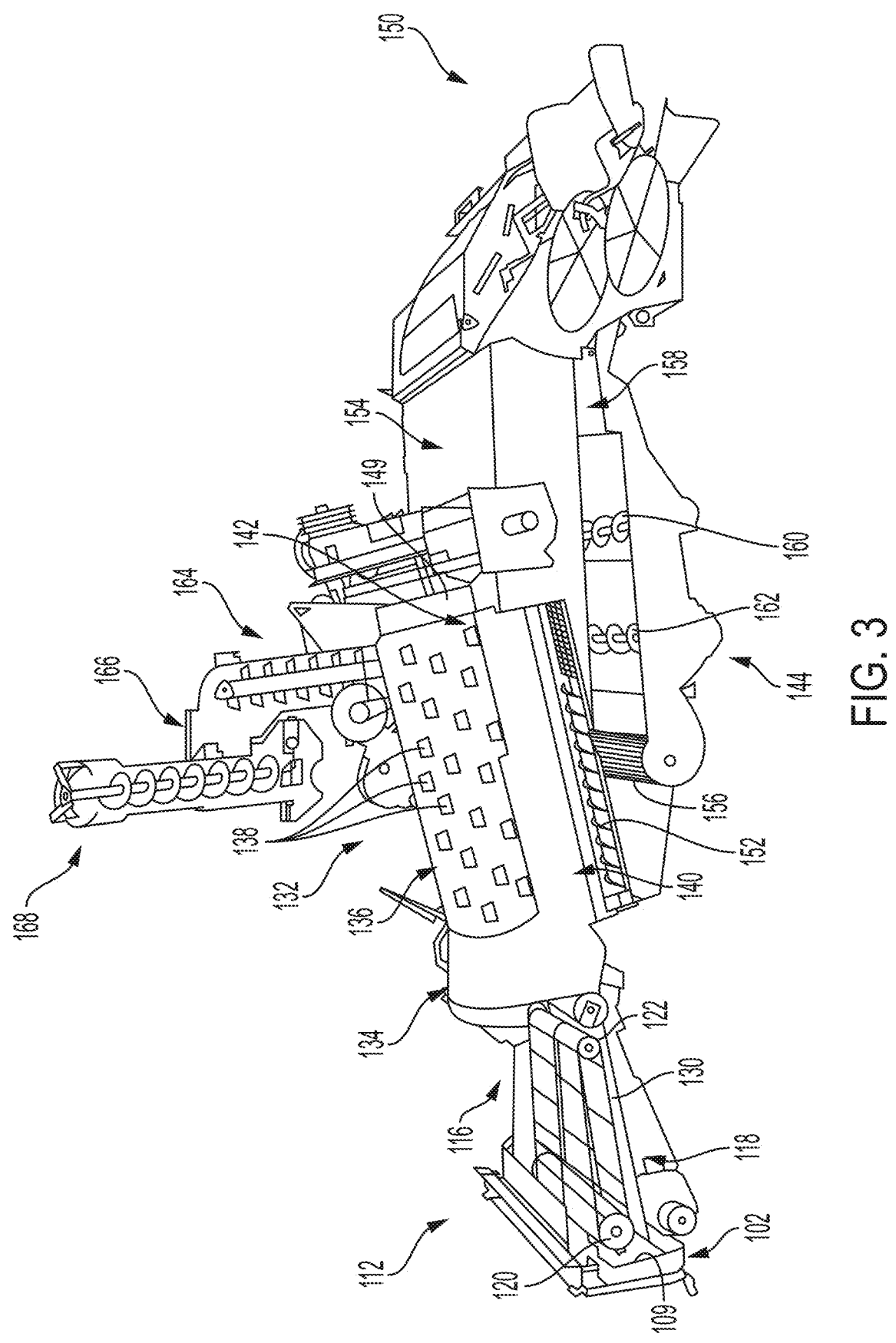
FIG. 3 is a fragmentary schematic view of the combine harvester.
Figure 4:
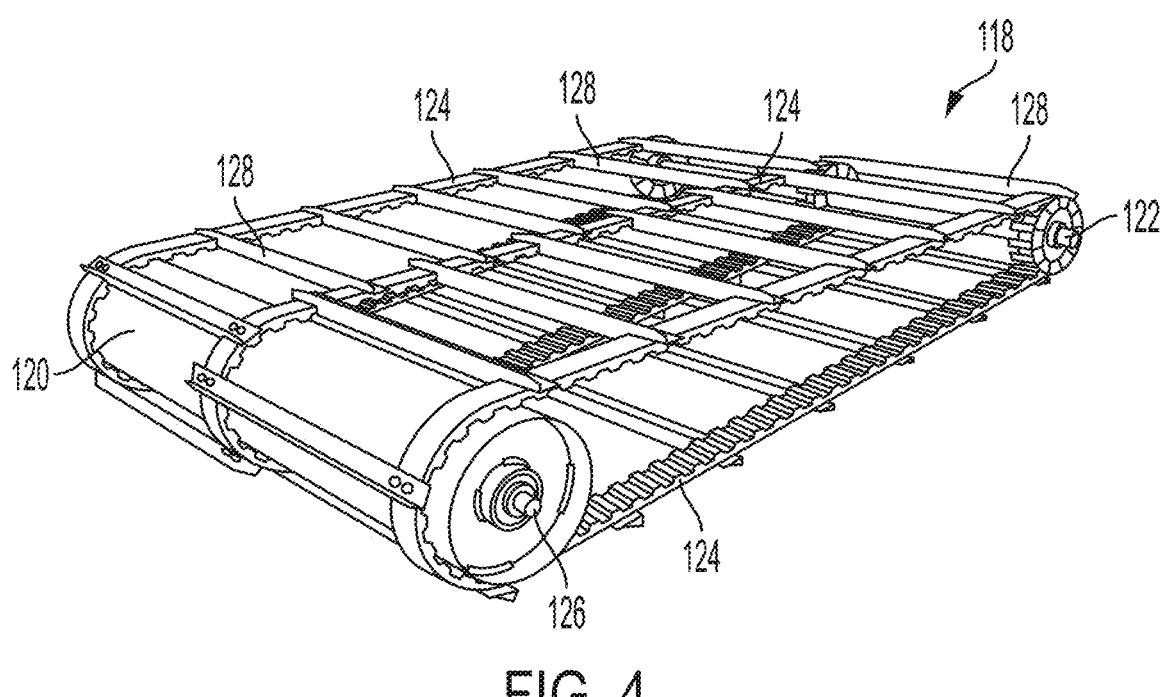
FIG. 4 is a perspective view of a conveyor of an example feeder unit that may be used with the combine harvester.

The feeder unit 112 of the combine harvester 100 is located generally between front tires 114 (only one is visible in FIG. 1) of the combine harvester 100 (and is supported by the frame of the combine harvester 100), and is configured to receive the cars of corn from the corn header 102 (and specifically, from the auger 110 thereof) and transport the cars of corn into the combine harvester 100. As shown in FIGS. 1 and 3-4, the feeder unit 112 includes (or generally defines) a channel 116 leading into the combine harvester 100, and a conveyor system 118 disposed generally within the channel 116 and configured to receive the cars of corn from the auger 110 of the corn header 102. The conveyor system 118 includes a drum 120 rotatably mounted to the combine harvester 100 toward a forward portion thereof (adjacent the corn header 102), and a drive shaft 122 mounted to the combine harvester 100 at a location rearward of the drum 120. Multiple straps 124 (e.g., bands, chains, belts, etc.) are coupled to the drum 120 (around the drum 120), and extend between the drum 120 and the drive shaft 122 of the conveyor system 118. The drive shaft 122, then, is configured to rotate (via a suitable motor, etc.) and cause movement of the straps 124 (e.g., via sprockets coupled to the drive shaft 122, etc.) around the drum 120 (whereby the drum 120 is configured to rotate about a central shaft 126 with the movement of the straps 124) (in a generally counterclockwise direction, as viewed in FIGS. 1 and 4).

The conveyor system 118 of the combine harvester 100 also includes multiple cross bars, or deflectors 128, coupled to the straps 124 between adjacent ones of the straps 124. The deflectors 128 are configured to move with the straps 124, as the straps 124 are moved by the drive shaft 122, generally along a length of the channel 116 of the feeder unit 112 and about the drum 120. In so doing, the deflectors 128 are configured to generally flatten the cars of corn (e.g., orient the cars of corn on their sides, orient the ears of corn to lie flat, etc.) as they are received from the corn header 102 under the drum 120, and push the cars of corn up the channel 116 of the feeder unit 112 (along a bottom wall 130 (or floor) of the channel 116 of the feeder unit 112) and into a threshing unit 132 of the combine harvester 100. In connection therewith, the conveyor system 118 (e.g., the drum 120, etc.) is moveable in a generally vertical direction relative to the combine harvester 100 (generally within the feeder unit 112). This allows for changing a height of a space under the conveyor system 118, for example, between the drum 120 and the bottom wall 130 of the channel 116 of the feeder unit 112 (and/or between the deflectors 128 and the bottom wall 130 of the channel 116), etc. (e.g., to accommodate the cars of corn (e.g., different types of cars of corn, different sizes of cars of corn, etc.), to optimize flow of cars of corn to the threshing unit 132, etc.).

Figure 5:
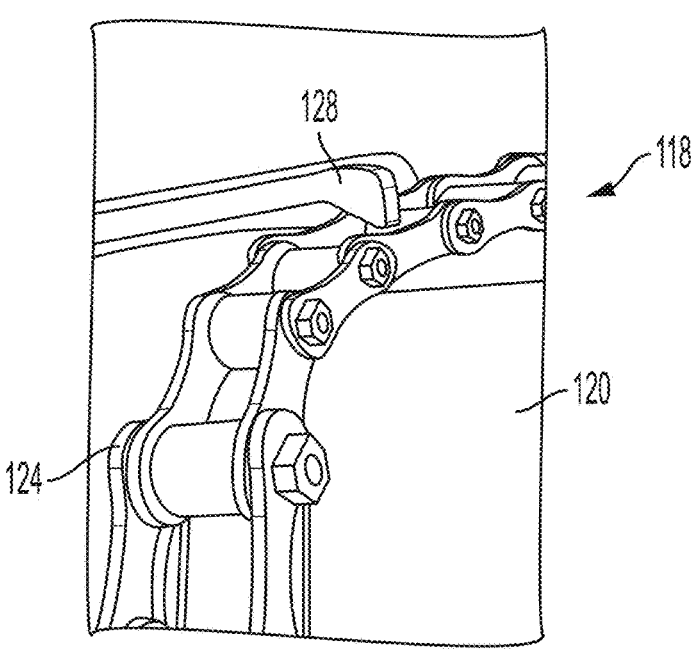
FIG. 5 is an enlarged, fragmentary perspective view of the conveyor of FIG. 4.
Figure 6:
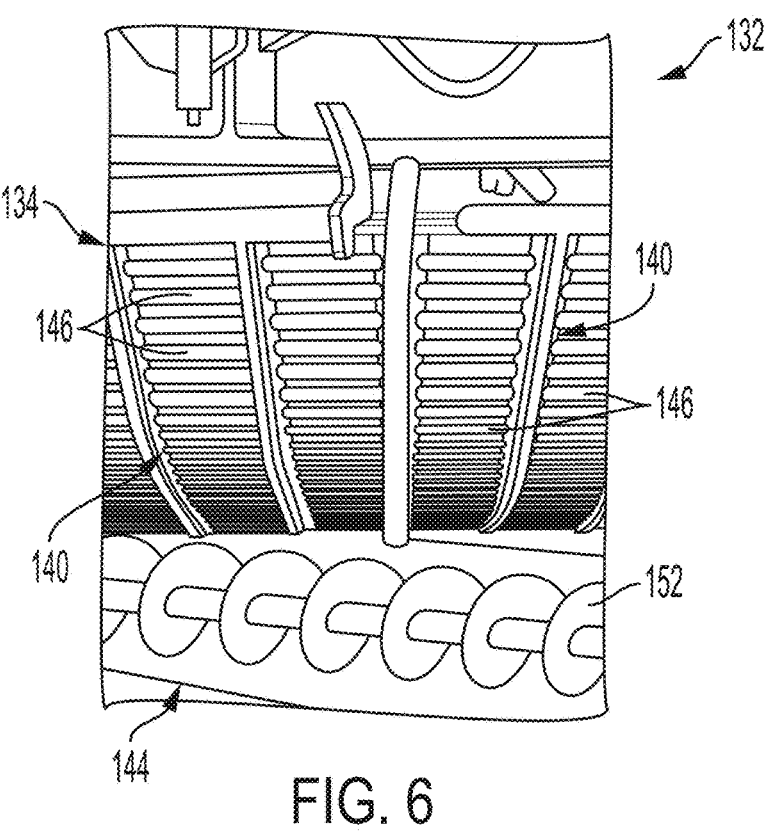
FIG. 6 is an enlarged, fragmentary perspective view of a housing (or rotor cage), and multiple separating grates associated therewith, of an example threshing unit that may be used with the combine harvester.

In the illustrated embodiment, the deflectors 128 of the conveyor system 118 are constructed from a material such as metal, rubber, or plastic, etc., having sufficient strength to push the cars of corn up the channel 116 of the feeder unit 112 to the threshing unit 132 but without damaging (or while inhibiting damage to) the corn kernels on the cars of corn. In addition in the illustrated embodiment, the deflectors 128 are constructed to have generally rounded edges (e.g., at locations where the deflectors 128 engage the cars of corn, or at locations where the deflectors 128 couple to the straps 124, etc.), to further help inhibit damaging the kernels on the cars of corn as the deflectors 128 push the cars of corn through the feeder unit 112. In one embodiment, for example, end portions of the deflectors 128 may be ground (e.g., where the deflector 128 attaches to the strap 124, etc.) to make a more rounded edge. Further, the straps 124 of the conveyor system 118 are constructed to also have generally rounded surfaces (e.g., at locations where the straps 124 may engage the cars of corn, etc.), to help inhibit damage to the kernels on the ears of corn as the cars are pushed by the deflectors 128 to the threshing unit 132. In one embodiment, for example, end portions of the straps 124 may be ground to make a more rounded edge. In the illustrated embodiment, the straps 124 include generally continuous bands (e.g., lugged belts, etc.). In other embodiments, the straps 124 may be configured otherwise (e.g., as links 124' (see, FIG. 5) with deflectors 128 coupled thereto, etc.).

As generally shown in FIGS. 1 and 3, the threshing unit 132 of the combine harvester 100 (as supported by the frame of the combine harvester 100) includes a cylindrical housing 134 (or rotor cage) extending generally from the forward portion of the combine harvester 100 to a rearward portion thereof, and a rotor 136 located generally within the housing 134. The threshing unit 132, then, is configured to receive the ears of corn from the feeder unit 112 into a forward portion of the housing 134, generally within a space (or spacing) defined between the housing 134 and the rotor 136. And, the rotor 136 is configured to rotate within the housing 134 and force the cars of corn (and any crop residue received with the cars of corn from the corn header 102) against the housing 134 (within the space between the rotor 136 and the housing 134). In this manner, the threshing unit 132 operates (by the mechanical action of pushing the cars of corn against the housing 134) to remove (or dislodge) the corn kernels from the cars of corn (and specifically, from the cobs of the cars of corn). With that said, the space between the housing 134 and the rotor 136, in the illustrated threshing unit 132, may range from about 10 mm (about 0.4 inches) to about 38 mm (about 1.5 inches), and may be generally consistent (or not) around the circumference of the rotor 136 and/or along the length of the housing 134. Further, the rotor 136 may be configured to rotate within the housing 134 at a speed of about 650 rpm or less (e.g., about 400 rpm or less, etc.).

The threshing unit 132 of the illustrated combine harvester 100 includes a single cylindrical housing 134 and rotor 136 for removing the corn kernels from the cars of corn. In other embodiments, though, combine harvesters may include threshing units with two (or more) cylindrical housings and corresponding rotors (with each rotor disposed within a corresponding one of the housings as generally described above), where the housings are located in the combine harvesters generally in parallel. In such embodiments, then, the housings and rotors are each configured in a similar manner to the housing 134 and rotor 136 described above to remove corn kernels from ears of corn received therein.

With additional reference to FIGS. 6-9, the rotor 136 of the threshing unit 132 includes multiple rasp bars 138 extending circumferentially around the rotor 136 (e.g., in a staggered cork-screw configuration, etc.) (FIGS. 1 and 3). The rasp bars 138 are each generally smooth and/or rounded in structure (e.g., to help inhibit damage to the corn kernels of the cars of corn as the cars are pushed through the housing 134, etc.). As the rotor 136 rotates within the housing 134, the rasp bars 138 are configured to engage the cars of corn (in the space between the rotor 136 and the housing 134) and move (e.g., push, etc.) the cars of corn (and crop residue) in a helical manner along the housing 134. In connection therewith, the housing 134 includes multiple concaves 140 and multiple separating grates 142 located along a lower portion of the housing 134. The concaves 140 and the separating grates 142 each include a combination of wires and/or bars that define openings therebetween (and, thus, that define openings within the concaves 140 and the separating grates 142). In connection therewith, as the rotor 136 moves the ears of corn through the housing 134, it also pushes the cars of corn against (and along) the wires and/or bars of the concaves 140 (e.g., in a first or forward part of the housing 134, etc.) and then against the wires and/or bars of the separating grates 142 (e.g., in a second or rearward part of the housing 134 following the first part, etc.), whereby the corn kernels are removed from (or separated from, or dislodged from, or knocked off) the cobs and pass through the concave openings and separating grate openings (along with other small material of the crop residue also pushed by the rotor 136 through the housing 134). The corn kernels and other small material then falls through, and below, the concaves 140 and the separating grates 142 generally downwardly and into a separating unit 144 of the combine harvester 100.

In the illustrated embodiment, the housing 134 of the threshing unit 132 includes three concaves 140 and three separating grates 142 (e.g., generally aligned side-by-side along a longitudinal axis of the housing 134, etc.). The first three concaves 140, located toward a forward part of the threshing unit 132 (e.g., toward the feeder unit 112), each include multiple rounded bars 146 (FIGS. 6 and 8) (e.g., having generally smooth circumferences, etc.) extending in a direction generally parallel to an axis of the housing 134. Each of the bars 146 of the first three concaves 140 has a diameter of about 0.75 inches, and the bars 146 are spaced laterally apart (e.g., generally equally, etc.) a distance of about 0.5 inches. Following the concaves 140 in the illustrated embodiment, the housing 134 then includes three separating grates 142, located toward the reward part of the threshing unit 132. The separating grates 142 each include slotted grates 148 (FIGS. 7 and 9) defining openings of about 0.75 inches by about 2 inches. With that said, it should be appreciated that a different number of concaves and/or separating grates may be included in threshing units of combine harvesters in other embodiments (e.g., more than three concaves, fewer than three concaves, more than three separating grates, fewer than three separating grates, etc.). For instance, in one embodiment, a combine harvester may include a threshing unit having a housing with four concaves and four separating grates, where the first four concaves toward a forward part of the threshing unit (e.g., toward a feeder unit of the combine harvester, etc.) each include multiple rounded bars and where the next four separating grates, toward the reward part of the threshing unit, then each include slotted grates. That said, it should be appreciated that other combinations of concaves and/or separating grates may be used in combine harvesters in other embodiments (e.g., combinations of concaves other than ones with rounded bars and separating grates with other than slotted grates, etc.).

As described above, as the cars of corn (and other crop residue) progress further through the housing 134 of the threshing unit 132, fewer corn kernels will be present on remaining cobs in the housing 134 to pass through the remaining concaves 140 (and/or remaining separating grates 142) (as the bulk of the corn kernels separated from the cobs will likely have already passed through the openings in the prior concaves 140). As such, the material remaining in the housing 134 at the later separating grates 142 will generally include the cobs and other larger crop residue (e.g., stalk fragments, leaves, husks, etc.). This remaining material is discarded from the threshing unit 132 through an outlet 149 at a rearward location of the housing 134, and into a discharge unit 150 (FIG. 3) of the combine harvester 100 where it is ejected back into to the field behind the combine harvester 100 (e.g., via a rotary beater, a grinder, a deflector, etc. of the discharge unit).

Figures 10, 11:
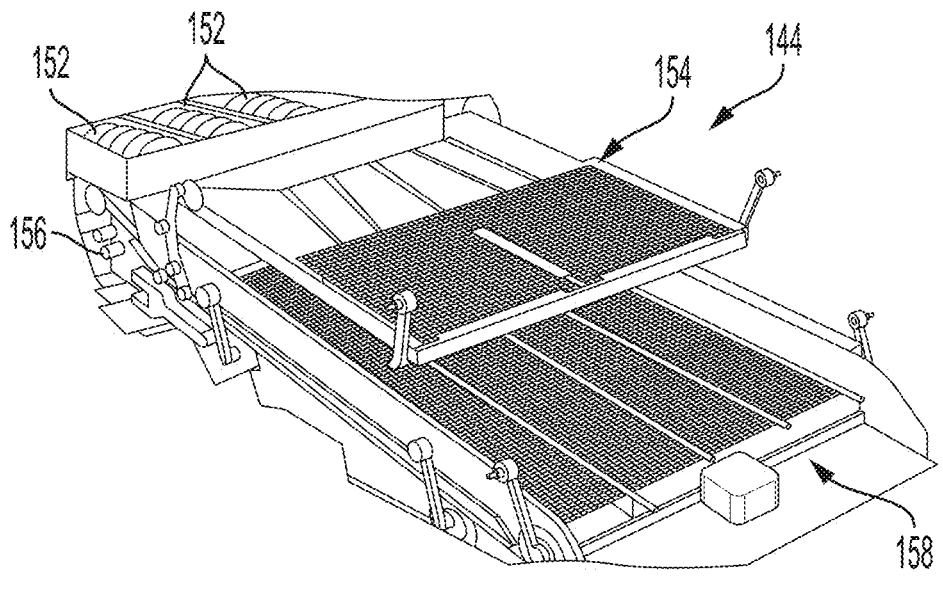
FIG. 10 is a perspective view of upper and lower sieves of the combine harvester.
FIG. 11 is a perspective view of an example storage hopper that may be included in the combine harvester.

As shown in FIGS. 3 and 10, the separating unit 144 of the combine harvester 100 is located generally below the threshing unit 132 (e.g., generally below the housing 134 and concaves 140 and separating grates 142 of the threshing unit 132, etc.) (and is supported by the frame of the combine harvester 100) and is configured to receive the corn kernels (and other small material from the crop residue) that pass through the concaves 140 and the separating grates 142 of the threshing unit 132 housing 134 (e.g., within a collection pan, etc.). Augers 152 are then configured to move or push the collected corn kernels and small material toward an upper sieve 154 (or chaffer) of the separating unit 144. And, a fan 156 of the separating unit 144 is configured to provide air flow to move or direct the corn kernels (and other small material) generally across the upper sieve 154. In addition, the upper sieve 154 is configured to reciprocate or otherwise move in a generally forward and reward direction (relative to the combine harvester 100) to facilitate movement of the kernels through apertures (or openings) in the upper sieve 154. In connection therewith, the apertures in the upper sieve 154 are sized to allow for the kernels to pass therethrough (and other similarly sized material from the crop residue that passed through the concaves 140, 142), but to block larger items (e.g., the apertures of the upper sieve 154 have sizes of about 15 mm (about 0.6 inches) to about 20 mm (about 0.8 inches) (e.g., ranges between about 0.5 inches and about 1 inch, etc.), etc.). The larger items that do not pass through the apertures, then, are pushed (e.g., by the fan 156, by the movement of the upper sieve 154, etc.) toward a rearward end of the upper sieve 154 where they are expelled from the combine harvester 100 (either directly, or via movement by an auger to the discharge unit 150). With that said, the fan 156 is configured to rotate (broadly, operate) at speeds between about 700 rpm and about 900 rpm in order to move the corn kernels toward and/or over the upper sieve 154 (along with any other small crop residue that passed through the concaves 140, 142).

A lower sieve 158 (or shoe sieve) is disposed generally beneath the upper sieve 154, in a position for receiving the corn kernels and other small material that pass through the apertures of the upper sieve 154. The lower sieve 158 is configured to reciprocate or otherwise move in a generally forward and reward direction (relative to the combine harvester 100) to then facilitate movement of the kernels through apertures (or openings) in the lower sieve 158. Fingers (or veins) extend generally upward from the lower sieve 158 at each of the apertures to help capture the kernels and generally direct them to the apertures. The apertures, here, are sized generally smaller than the apertures of the upper sieve 154 to accommodate the sizes of the corn kernels and allow for the kernels to pass therethrough, but to block other larger residue. For instance, the apertures in the lower sieve 158 may range in size from about 5 mm (about 0.2 inches) to about 15 mm (about 0.6 inches).

Material that is blocked from passing through the apertures of the lower sieve 158 is pushed (e.g., again by the fan 156, by the movement of the lower sieve 158, etc.) toward a rearward end thereof where it is collected. And, a tailings auger 160 is configured to then carry the collected material (that passed through the upper sieve 154 but not the lower sieve 158) to one side of the combine harvester 100 where a tailings elevator is configured to carry the collected material back to an inlet of the threshing unit 132 for further processing (e.g., to capture any corn kernels that may still remain on cobs of cars of corn, etc.).

Finally, with reference to FIG. 11, corn kernels that pass through the lower sieve 158 are collected there below and are transported, by an auger 162, to an elevator 164 that then carries the kernels to a hopper 166 (on the combine harvester 100) for storage (as supported by the frame of the combine harvester 100). The elevator 164 generally includes a drive shaft configured to actuate multiple lifts (e.g., paddles, buckets, etc.) (via a chain coupled to the lifts) to carry (or lift, etc.) the collected corn kernels from the auger 162 to an auger 170 that then deposits the corn kernels in the hopper 166 for temporary storage. When the hopper 166 is filled with corn kernels, a chute 168 of the combine harvester 100 is moved outward and augers 172, 174 (disposed generally in a bottom portion of the hopper 166) are configured to direct the kernels to (and converge the kernels at) the chute 168. To do so, the augers 172, 174 are configured to rotate, to direct the kernels to the chute 168, where another auger within the chute 168 moves the kerns along the chute 168 (see, FIG. 1) for deposit in a desired container (e.g., dump cart, a truck, a wagon, etc.).

Figure 13:
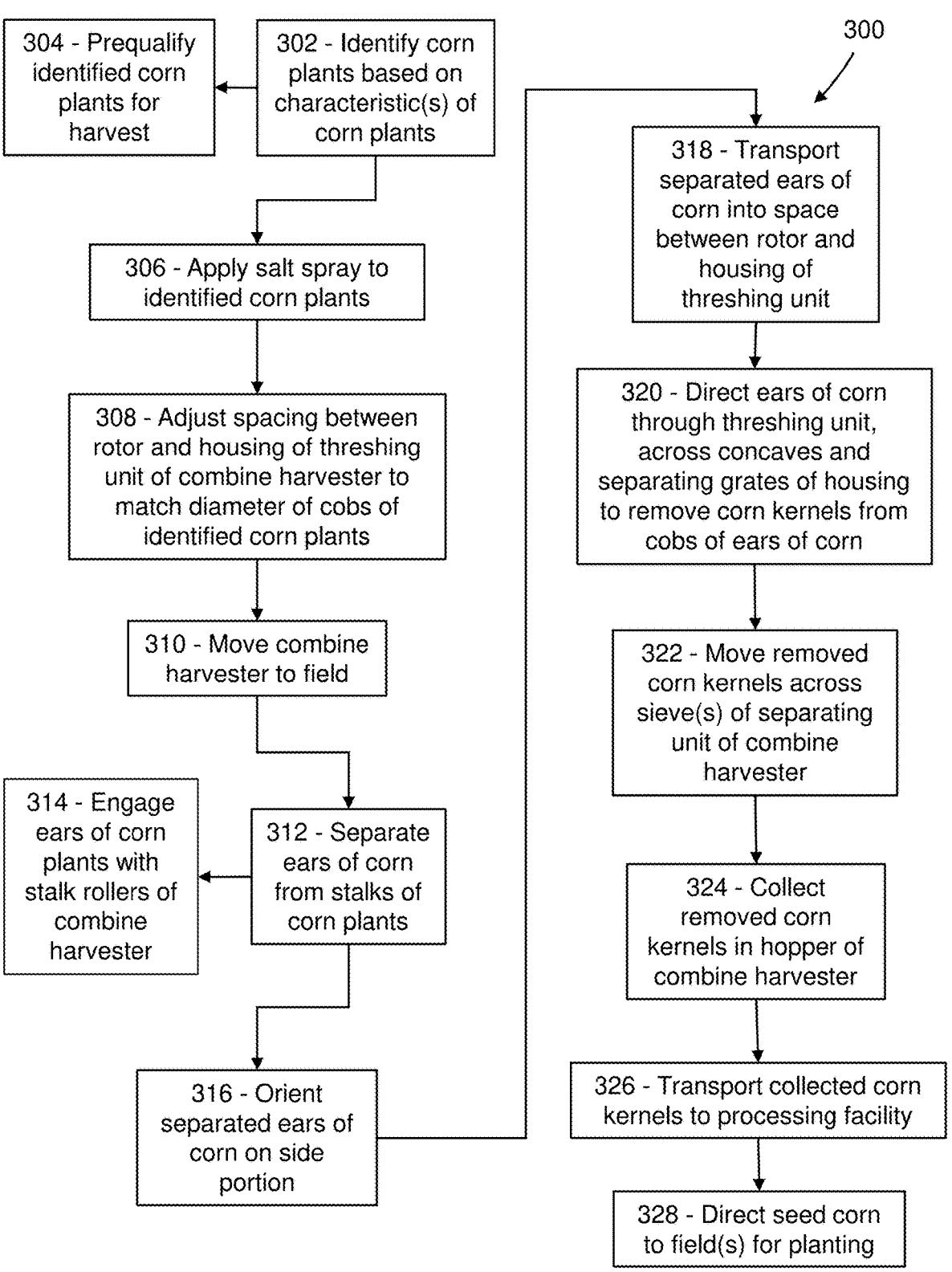
FIG. 13 illustrates an example method for producing seed corn for use in growing corn plants, using the combine harvester of FIG. 1.

An example operation of the combine harvester 100 to collect (or harvest) corn kernels from corn plants in a desired (or selected or identified) field, as part of a seed corn production process, will be described next (with reference also made herein to example method 300 of FIG. 13). As described below, the corn plants may be identified based on particular characteristics of the corn plants (e.g., at 302 in method 300), whereby the identified corn plants may be prequalified (e.g., at 304 in method 300) for harvest based on the particular characteristics. In connection therewith, in some examples, salt spray may be applied (e.g., at 306 in method 300) to the identified (and/or prequalified) corn plants. Thereafter, the combine harvester 100 is moved (e.g., at 310 in method 300) to the desired field for harvesting and is positioned in the field so that rows of corn plants in the field are in alignment between adjacent row dividers 104 of the corn header 102 of the combine harvester 100. The combine harvester 100 is then operated (e.g., moved, driven, etc.) through the field at a rate (or speed) of about 3.5 miles per hour (mph) (e.g., as a manageable rate for operating the combine harvester 100 in the field and/or as an identified rate to provide a desired flow of corn plants into the corn header 102 for processing, etc.) (and as compared to much faster rates (e.g., greater than 5 mph, etc.) at which conventional combine harvesters are operated to harvest fields in order to maximize field coverage in a short amount of time). In connection therewith, the stalk rollers 108 of the corn header 102 are operated at a speed of about 1,120 rpm, in order to separate (e.g., at 312 and 314 in method 300) the ears of corn from the stalks of the corn plants as the corn plants are received between the row dividers 104. This particular speed of the stalk rollers 108 allows or enables the corn header 102 to effectively match the rate at which corn plants are received by the corn header 102 based on the operating rate of the combine harvester 100 of about 3.5 mph (and to remove the ears of corn from the corn plants at a rate that helps inhibit the stalk rollers 108 from clogging with multiple corn plants and/or removing ears of corn too quickly whereby the ears may not be received into the separation chambers 106, etc.).

Once the cars of corn are removed from the corn plants, they are directed by the auger 110 of the corn header 102 to the feeder unit 112. In so doing, the auger 110 of the corn header 102 may be elevated (or raised) so that the cars of corn flow generally under the auger 110 with little or minimal impact (or even no impact in some embodiments) from the auger 110 (e.g., to help inhibit a pinching of the cars of corn between the auger 110 and a trough portion of the corn header 102 generally below the auger 110 and along which the cars of corn move, to help inhibit damage to the corn kernels on the cars by way of contact of the auger 110 against the corn kernels, etc.). In so doing, the subsequent inflow of cars of corn from the separation chambers 106 of the corn header 102 (and other plant material, fodder, etc.) may help push the earlier removed ears of corn generally under the auger 110 (with some, little, or no help from the auger 110) and to the feeder unit 112 (e.g., whereby the cars of corn generally flow from the stalk rollers 108 to the feeder unit 112 based (at least in part) on forces of additional cars of corn (and fodder, etc.) consistently received into the separation chambers 106 of the corn header 102 through the particular operating speed of the combine harvester 100 and stalk rollers 108 described above, etc.).

At the feeder unit 112, in order to accommodate the ears of corn, the drum 120 of the conveyor system 118 is generally elevated relative to the bottom wall 130 of the channel 116 of the feeder unit 112, for example, to provide sufficient space for the ears of corn to move generally thereunder (as they are pushed by the generally consistent inflow of ears of corn being received from the corn header, again through the particular operating speed of the combine harvester 100 and stalk rollers 108 described above, etc.). As such, the ears of corn received from the corn header 102 generally flow through the feeder unit 112 with little or minimal impact (or even no impact in some embodiments) from the deflectors 128, to the threshing unit 132 (e.g., to help inhibit damage to the corn kernels on the ears by way of contact of the deflectors 128 against the corn kernels, etc.). For example, the drum 120 of the conveyor system 118 may be elevated to a maximum setting above (or all the way above) the bottom wall 130 of the conveyor system 118 to provide room for the ears of corn to move (or flow) under the drum 120, but to still allow for the deflectors 128 to potentially engage the ears of corn and help move them through the feeder unit 112 and orient them on their sides (e.g., at 316 in method 300) (as needed in some embodiments). In addition, a deflecting panel may be positioned generally above the drum 120, for example, to help guide the ears of corn under the drum 120 (and potentially inhibit ears of corn from passing over the drum 120, etc.). The feeder unit 112 then delivers the ears of corn to the inlet of the threshing unit 132 (e.g., allows the ears of corn to flow into the threshing unit 132 with little or no added force from the deflectors 128 (which may damage the corn kernels on the ears), etc.), were the ears are received into the housing 134 of the threshing unit 132 and the corn kernels are separated from the cobs of the ears.

At the threshing unit 132, the space between the housing 134 and the rotor 136 (and more specifically, the space between end portions of the rasp bars 138 of the rotor 136 and surfaces of the concaves 140 and separating grates 142 (when the rasp bars 138 are generally at their closest points to the concaves 140 and the separating grates 142), etc.) is set at about 20 mm (about 0.8 inches) (generally uniformly around the housing 134 of the threshing unit 132 and generally uniformly along a length of the housing 134) (broadly, a concave setting of between about 18 mm (about 0.7 inches) and about 24 mm (about 0.94 inches), etc.) (e.g., at 308 in the method 300). This spacing allows the ears of corn to flow into the threshing unit 132, between the housing 134 and the rotor 136 (e.g., at 318 in the method 300), without interference from the rotor 136 and without requiring additional force from the deflectors 128 of the feeder unit 112 to push or shove the ears of corn therein. In addition, this spacing is generally larger than normal, relative to a size (or diameter) of a cob of an ear of corn entering the threshing unit 132 (e.g., where an ear corn cob (not accounting for the corn kernels) may have a diameter of about 20 mm (about 0.8 inches), etc.), such that a concave setting here of about 20 mm (0.8 inches) generally matches (or about matches) a diameter of the seed corn cob of the corn plants being harvested by the combine harvester 100). In other words, this spacing generally allows the ears of corn to flow into the threshing unit 132 under their own flow, from the feeder unit 112 (generally between a body of the rotor and the concaves 140) (as they are pushed by the generally consistent inflow of ears of corn being received from the corn header 102, again through the particular operating speed of the combine harvester 100 and stalk rollers 108 described above and the particular setting of the drum 120 of the conveyor system 118, etc.), and then provides ability of the rasp bars 138 to engage the received ears of corn and push them against the concaves 142 and separating plates 142 (since a diameter of the ears of corn still having the kernels attached to the cobs would generally still be larger than the concave setting). Additionally in this embodiment, end portions of the rounded bars 146 of the first concave 140 are generally flattened (e.g., ground, etc.) to provide for a smooth ramp surface 176 for the ears of corn to flow into the housing 134.

The rotor 136, then, is configured to rotate within the housing 134 of the threshing unit 132 at a relatively slow speed of about 350 rpm (broadly, between about 200 rpm and about 400 rpm). In doing so, the ears of corn are generally slowly (or gently) agitated in the housing 134, and the corn kernels are removed from (or separated from) the cobs of the ears of corn (as the rotor 136 pushes the ears of corn along and against the concaves 140 and separating grates 142 of the housing 134) (e.g., at 320 in method 300), and the kernels pass through the openings in the concaves 140 and the separating grates 142. The separated corn kernels are collected at the separating unit 144 below the threshing unit 132.

In the separating unit 144, the fan 156 is operated at a speed of about 850 rpm in order to help move and/or direct the corn kernels (and any other small crop residue that passed through the concaves 140, 142) across the upper sieve 154 (e.g., at 322 in the method 300). This relatively low speed generally accounts for the smaller size and weight of seed corn being processed herein (e.g., as compared to the larger size and/or heavier weight of No. 2 yellow corn typically harvested by combine harvesters, etc.), and helps inhibit the fan 156 from inadvertently pushing the corn kernels across the upper sieve 154 too quickly (whereby the corn kernels are unable to fall through the openings of the upper sieve 154).

That said, the upper sieve 154 of the separating unit 144 has multiple openings (or apertures) defined therein, having sizes of about 18 mm (about 0.7 inches) toward a forward part of the sieve 154, about 17 mm (about 0.67 inches) toward a middle part of the sieve 154, and about 18 mm (about 0.7 inches) toward a rearward part of the sieve 154. As such, as the corn kernels and other material move across the upper sieve 154, the corn kernels pass through the openings of the upper sieve 154 (along with some crop residue sized smaller than the openings of the sieve 154), and fall to the lower sieve 158. The lower sieve 158 then also has multiple openings (or apertures), each having sizes of about 7 mm (about 0.3 inches), whereby only the corn kernels are intended to pass through the lower sieve 158 for collection. Each of the openings of the lower sieve 158 is associated with a finger (or vein) having a length of about 1.125 inches extending generally upward from the lower sieve 158 to help capture the kernels and generally direct them to the corresponding openings. In this example operation, the tailings elevator is opened (e.g., a door, etc. of the tailings elevator is opened, etc.), or is provided with such an opening, so that the crop residue collected from the lower sieve 158 (i.e., the crop residue that passed through the upper sieve 154 but not the lower sieve 158) is discharged from the combine harvester 100 (at the rearward end of the combine harvester 100), instead of being recycled back to the threshing unit 132 (as is conventional) (as any corn kernels still present in the crop residue are not reintroduced to the threshing unit 132 to avoid disturbing the consistent flow of cars of corn thereto from the feeder unit 112 and to also avoid introducing potentially damaged kernels of corn thereto).

Finally, corn kernels that pass through the lower sieve 158 are collected there below and are directed (by the auger 162) to the elevator 164, which then carries the kernels to the hopper 166 (on the combine harvester 100) for storage (e.g., at 324 in method 300). In so doing, the elevator 164 is operated at a relatively low speed of about 350 rpm (e.g., via use of a 20-tooth sprocket installed at the drive shaft of the elevator 164 to then operate the chain driven buckets of the elevator 164, etc.). This speed generally allows the corn kernels received through the lower sieve 158 to be transferred to the hopper 166 at a generally consistent rate, that generally matches the inflow of corn kernels from the lower sieve 158 (again, which is essentially based on the flow of ears of corn into the combine harvester 100 (resulting from the particular operating speeds of the combine harvester 100 and stalk rollers 108 described above, and the particular settings of the conveyor system 118 and feeder unit 112 also described above), etc.).

A sensor is provided in the hopper 166 below a top portion of the augers 172, 174 therein. The sensor is configured to activate the augers 172, 174 (or provide a warning to an operator of the combine harvester 100) when the corn kernels in the hopper 166 reach a height associated with the sensor. As such, the augers 172, 174 are configured to activate and direct the corn kernels in the hopper 166 to the chute 168 for discharge before the hopper 166 substantially fills with corn kernels (and before the augers 172, 174 themselves are covered with corn kernels). In doing so, the augers 172, 174 are configured to each rotate at a relatively slow speed of about 1,400 rpm to direct the kernels to the chute 168 (e.g., via larger sprockets 178 coupled to drive shafts thereof, etc.), where the kernels are then transferred by the chute 168 from the combine harvester 100 to another container (e.g., a truck, a cart, etc.). It should be appreciated that in one or more embodiments, the container to which the corn kernels are transferred does not include an auger (e.g., the container will not include an auger cart, etc.).

Figure 12:
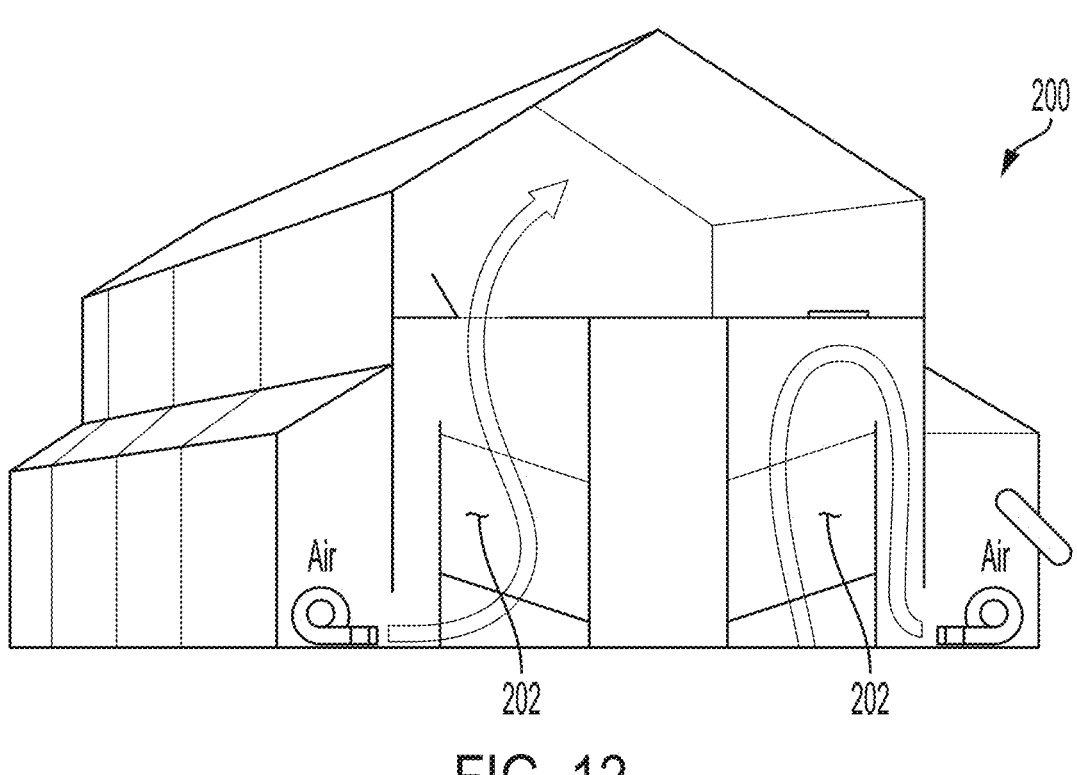
FIG. 12 is a schematic view of a dryer unit that may be used for drying corn kernels harvested by operation of the combine harvester of FIG. 1, as described herein, for subsequent storage as bulk dry shell seed corn.

In turn, the corn kernels collected from the combine harvester 100 are transferred to a processing facility (e.g., at 326 in method 300) where they are dried in a drier and then, once dry, stored as bulk dry shell seed corn (in this example) (e.g., for planting at 328 in method 300). FIG. 12 illustrates an example corn ear drier 200 that may be used to dry the corn kernels collected from the combine harvester 100. Batches of corn kernels to be dried are positioned in chambers 202 of the corn ear drier 200 (e.g., on one or more layered drying surfaces, etc.). And, the corn kernels are arranged in batches in the chambers 202 to help facilitate all of the corn kernels in the batches having substantially the same moisture content. For instance, and without limitation, the corn kernels may be arranged in batches having width dimensions of about 25 feet, length dimensions of about 25 feet, and height (or thickness) dimensions of about 4 feet, etc. That said, the corn ear drier 200 may be configured to process upwards of about 2,500 bushels of seed corn every 12 hours (or upwards of about 210 bushels of seed corn an hour).

In connection therewith, at the processing facility, the corn kernels are dried in the corn ear driers at temperatures of less than about 110° F. (e.g., at temperatures between about 95° F. and about 105° F., etc.) to a moisture content of about 14% or less (e.g., about 12%, about 13%, etc.). Such drying may take between about 10 hours and about 25 hours, for example, depending on the moisture content of the corn kernels harvested from the field (e.g., which may be between about 15% and about 25% (e.g., about 25% or less, about 19% or less, etc.) in the above example, etc.) and the desired final moisture content of the corn kernels (e.g., which may be between about 12% and about 14%, etc.). As can be appreciated, when the corn kernels are harvested from the field at a lower moisture content, less time may be required to dry the corn kernels to the final desired moisture content. Once dried, the corn kernels are cleaned (as needed) and stored in a conventional manner for subsequent use, for example, as seed corn, etc. And, the seed corn may then be used to grow additional corn plants such as, for example, those used to produce No. 2 yellow corn (which may then be subsequently harvested and used as feed corn, to product ethanol, etc.).

In various embodiments, the combine harvester 100 may also be configured to provide notifications to users thereof (directly on-board the combine harvester 100, to remote users, etc.) regarding operational parameters of the combine harvester 100 (e.g., operational speeds of one or more of the augers in the combined harvester 100, operational speeds of the stalk rollers 108, operational speeds of the rotor 136, spacings between the rotor 136 and the housing 134, operational speeds of the fan 156, a travel speed of the combine harvester 100, a flow rate of corn through the combine harvester 100, etc.). In addition, the combine harvester 100 may be configured to modify or adjust one or more of the operational parameters of the combine harvester 100 based on preset limits or parameters to ensure desired operation.

As kernels of corn plants harvested in accordance with the systems and methods herein may have lower moisture contents (e.g., between about 15% and about 25% etc.), than kernels of corn plants harvested by conventional ear pickers, less time and resources may be required to dry the kernels of corn to desired moisture contents (e.g., which may be between about 12% and about 14%, etc.). For instance, as noted above, drying kernels of corn harvested in accordance with the systems and methods herein to such desired moisture contents may take between about 10 hours and about 25 hours (e.g., about 25 hours or less, about 15 hours or less, about 11 hours or less, about 10 hours, etc.). By contrast, drying entire cars of corn harvested by conventional ear pickers may take upwards of 80 hours or more. What's more, by way of the present disclosure, additional shelling operations are not required to obtain the kernels of corn (as would still be required for the dried ears of corn harvested by conventional car pickers).

By way of the above example operation of the combine harvester 100, a generally consistent flow of corn is provided to and through the combine harvester 100 for processing (to form seed corn). For example, operating the combine harvester at the rate of about 3.5 mph together with operating the stalk rollers 108 of the corn header 102 at the speed of about 1,120 rpm provides a particular flow of cars of corn into the combine harvester, which is then matched by the particular operating parameters identified above for the feeder unit 112, threshing unit 132, separating unit 144, elevator 164, and augers 172, 174, etc. As such, the particular parameters identified above, in combination, provide for the consistent flow of material to and through the combine harvester 100, thereby essentially keeping the combine harvester 100 (and each of the units, components, etc. therein) full of such material during the operation. This, in turn, helps inhibit damage to the corn kernels as they pass through the combine harvester.

In addition, by the above example operation, a time from which the cars of corn are picked by the combine harvester 100 to a time the kernels are stored as seed corn may take about 25 hours or less. This is significantly quicker than the time required for similar operations using corn ear pickers (which can take upwards of 80 hours or more to complete from the time the cars of corn are picked to the time the kernels are removed from the cars and stored as seed corn). What's more, fewer resources are required to subsequently process the separated kernels (as compared to processing intact cars of corn provided from conventional corn ear pickers), not only in the elimination of the need for separate de-husking and shelling equipment but also in the need of fewer transport trucks, fewer driers (and shorter dry times, as discussed more below), etc. As such, a substantial savings in costs may be realized by implementation of the combine harvester 100, in the manner described, to harvest corn plants in connection with seed production processes or programs (e.g., where the collected corn kernels are subsequently used as seed to grow further corn plants, etc.).

In various implementations of the above operation, the field in which the combine harvester 100 is directed for harvesting corn plants (as part of the seed corn production process, for example) may be selected based on moisture content of the corn kernels of the corn plants in the field. In connection therewith, it has been found that harvesting corn plants in which the corn kernels have moisture contents of about 25% or less (e.g., between about 15% and about 25% (e.g., about 19%, etc.), etc.), in accordance with the above example operation of the combine harvester 100 (to product seed corn), may improve corn kernel yield from the harvested corn plants as well as quality of the resulting corn kernels (e.g., it may inhibit damage to and/or loss of corn kernels, etc.) (e.g., as compared to harvesting the corn plants at a similar moisture contents using conventional corn ear pickers, etc.). In particular, the inventors hereof have found that harvesting corn plants in which the corn kernels have moisture contents exceeding 25%, using combine harvesters in general, has a negative impact on both cold and warm germination (or viability) of the corn kernels (even though such higher moisture contents are advantageous when harvesting with corn ear pickers). For instance, at moisture contents above 25%, the corn kernels are more tightly attached to the cobs, thus requiring more aggressive rotor speeds in the threshing units of the combine harvesters and/or smaller concave settings (e.g., smaller spacings between the concaves and the rotors, etc.) in order to remove the corn kernels from the cobs. However, this can result in damage to the corn kernels, or an ineffective removal of the corn kernels from the cobs. At moisture contents of less than about 25%, though, the inventors hereof have found that the kernels can be removed from the cobs with less effort, for example, within the threshing unit 132 of the combine harvester 100 (in the manner described above), and thus with less damage to the kernels.

Tables 1 and 2 illustrate results from an example operation of the combine harvester 100, in harvesting corn plants at three different moisture contents (i.e., about 23.8%, about 20.5%, and about 18.9%). In so doing, three samples of corn plants were analyzed at each of the three different moisture contents. As shown in Table 1, both cold and warm germination of the resulting corn kernels were highest for the samples at which the moisture content, at harvest, was about 18.9%. Lower cold germination and warm germination rates were exhibited for corn plants harvested at higher moisture contents (which, in some examples, may not satisfy certain defined benchmarks, etc.). And, as shown in Table 2, percentages of corn kernels recovered (i.e., corn kernel yield) from the harvested corn plants were highest for the samples at which the moisture content, at harvest, was about 18.9%.

TABLE 1

| Harvest Moisture Content | Cold Germination | Warm Germination |
|---|---|---|
| 23.8% | 68% | 75% |
| 20.5% | 85% | 94% |
| 18.9% | 96% | 98% |

TABLE 2

| Harvest Moisture Content | Recovered Seed (Yield) |
|---|---|
| 23.8% | 95.3% |
| 20.5% | 96.2% |
| 18.9% | 97.7% |

Table 3 illustrates example allowable visible damage as achieved in connection with the above operation of the combine harvester 100, in harvesting corn plants at different moisture contents ranging from about 12% to about 19%. As shown, visible damage (as a percentage of seeds harvested from a field) to the resulting corn kernels generally decreased as the moisture content, at harvest, decreased (e.g., visible cracks in the corn kernels after exposure to an iodine solution decreased, etc.).

TABLE 3

| Harvest Moisture Content | Mechanical Damage (Visible) |
|---|---|
| 19% | 6% |
| 18% | 5% |

TABLE 3-continued

| Harvest Moisture Content | Mechanical Damage (Visible) |
|---|---|
| 17% | 4% |
| 16% | 4% |
| 15% | 3% |
| 14% | 3% |
| 13% | 2% |
| 12% | 2% |

With that said, an example operation for measuring moisture content of corn kernels of corn plants in a field, in connection with determining whether or not to harvest the corn plants in the field (for seed corn) by way of the above example operation of the combine harvester 100, is described next. Here, the moisture content of the corn kernels is measured using near-infrared spectroscopy (wherein moisture in the corn kernels absorbs certain wavelengths of light and wherein the amount of such wavelength absorption provides an indication of the amount of moisture in the corn kernel). In particular, in measuring the moisture content of the corn kernels, a portable device (e.g., as available from Perten Instruments, etc.) is used to obtain multiple measurements from at least three different locations in the field (e.g., at least about 24 measurements at each location, etc.). Then, in this example, when at least 90% of the measurements at each location indicate that the corn plants in the field have moisture content readings of about 19% or less, the field is designated to be harvested by the combine harvester 100. If this benchmark value of 19% is not satisfied, the corn kernels are allowed to further dry and subsequent testing operations may be performed until at least 90% of the measurements indicate that the corn kernels of the corn plants in the field have moisture content readings of about 19% or less. That said, it should be appreciated that in other examples, the benchmark moisture content utilized in connection with determining whether or not to harvest corn plants in a field by way of the above example operation of the combine harvester 100 may be different than 19%. For instance, the benchmark moisture content may be a moisture content that is less than about 25%, a moisture content of about 23%, a moisture content of about 22%, a moisture content within a range of about 15% to about 25%, particular values and/or ranges therebetween, etc.).

As described above, harvesting corn plants by way of the above example operation of the combine harvester 100 (to produce a bulk supply of seed corn), at the moisture contents of about 25% or lower (e.g., about 19%, etc.), may provide for improved germination of the resulting corn kernels. As such, through the above operation, the combine harvester 100 may be viewed as generally preserving or protecting germination viability of the resulting corn kernels harvested thereby, in that a predominant number of harvested corn kernels (e.g., greater than about 50% (in general) of the corn kernels harvested from a field by the combine harvester 100, greater than about 70% of the corn kernels harvested from a field by the combine harvester 100, greater than about 80% of the corn kernels harvested from a field by the combine harvester 100, greater than about 90% of the corn kernels harvested from a field by the combine harvester 100, etc.) (as a defined benchmark, etc.) remain viable after harvesting and can be grown from the corn kernels into corn plants (e.g., into corn plants used to product No. 2 yellow corn, etc.).

For instance, in one example, through the above operation, the combine harvester 100 may be viewed as generally preserving or protecting germination viability of the resulting corn kernels harvested thereby, in that greater than about 75% (e.g., at least about 80% or greater, at least about 84% or greater, etc.), for cold germination, of the corn kernels harvested from a field by the combine harvester 100 remain viable after harvesting and can be grown from the corn kernels into corn plants (e.g., into corn plants used to product No. 2 yellow corn, etc.). In connection therewith, the cold germination rate generally represents seed viability under less than optimum growing conditions, such as those that may occur in a field (e.g., wet/cold environments, etc.), and generally represents seed vigor. For instance, an example test for cold germination includes growing seeds in a lab environment at about 60° F. or less, for 5-7 days, and then counting seeds that germinate (e.g., of a representative sample of 100 such seeds, etc.). In another example, through the above operation, the combine harvester 100 may be viewed as generally preserving or protecting germination viability of the resulting corn kernels harvested thereby, in that greater than about 75% (e.g., at least about 90% or greater, at least about 94% or greater, at least about 95% or greater, etc.), for warm germination, of the corn kernels harvested from a field by the combine harvester 100, etc.) remain viable after harvesting and can be grown from the corn kernels into corn plants (e.g., into corn plants used to product No. 2 yellow corn, etc.). In connection therewith, the warm germination rate generally represents seed viability under optimum conditions and generally represent maximum germination levels. An example test for warm germination includes growing seeds in a lab environment at about 77° F., for 5-7 days, and then counting seeds that germinate (e.g., of a representative sample of 100 such seeds, etc.).

With that said, in connection with harvesting corn plants at moisture contents of about 25% or less (e.g., about 19% or less, etc.) to produce a bulk supply of seed corn, the corn plants must remain in the field longer in order to achieve the lower moisture content (as compared to harvesting the corn plants using conventional corn ear pickers, at which the corn plants can be harvested earlier at higher moisture contents between about 32% and about 38%). This additional time over which the corn plants remain in the field may be upwards of about two to three weeks (e.g., about 14 days to about 21 days, etc.), and may extend into colder seasons in some regions. In that time, as can be appreciated, risks may increase for damage to the corn plants (e.g., weather damage, bug damage, mold damage, etc.). As such, while certain improvements may be achieved by use of the combine harvester 100 herein (as described above), in harvesting corn plants when the moisture contents of the corn kernels of the corn plants is about 25% or less, substantial added risks are also present in the extended time the corn plants must remain in the fields before they are harvested.

In connection with the above implementations of the combine harvester 100, in one or more embodiments the field in which the combine harvester 100 is directed for harvesting corn plants (as part of the seed corn production process) may further be prequalified (or predetermined) based on one or more characteristics of the corn plants in the field (whereby moisture content of the prequalified corn plants may then be monitored in the example manner described above, in order to achieve the benchmark moisture content of about 25% or less, etc.). In such implementations, if the corn plants in the field do not satisfy the one or more characteristics, the corn plants may instead be harvested by way of conventional processes (e.g., by use of corn ear pickers at higher moisture contents of about 32%, etc.). Characteristics that can be used to prequalify corn plants for harvesting by the combine harvester 100, in the manner described herein, may include one or more of size and/or shape of corn kernels of corn plants, strength of stalks of the corn plants, and/or types of the corn plants, etc.

For instance, corn plants having corn kernels with generally larger sizes (e.g., seeds classified as large round (AR2), etc.) have been found to exhibit lower germination percentages, in general. As such, in some examples, fields having corn plants with such larger corn kernels may not be selected (or prequalified) for harvesting by way of the above operations. Similarly, corn kernels having generally rounded shapes (verses generally flat shapes) have been found to exhibit more visible damage following harvesting by the combine harvester 100 (e.g., such seeds may bounce around more in the combine harvester 100 during processing, etc.). As such, in some examples, fields having corn plants with such generally round corn kernels (e.g., corn plants having about 40% or more round corn kernels, etc.) may not be selected (or prequalified) for harvesting by way of the above operations. Instead, in such fields having corn plants with larger corn kernels and/or corn kernels with generally rounded shapes, the fields may be harvested by conventional corn ear pickers, at conventional moisture contents of about 32% to about 38%.

In addition, certain hybrids of corn plants that are known to be suitable for or receptive of salt spray (e.g., Defol®, etc.) may be selected (or prequalified) for harvesting by way of the above operations, to allow for increasing dry down rates of the corn plants in the field (e.g., to help achieve moisture contents of about 25% or less sooner than naturally waiting, etc.) and help expedite harvesting of the corn plants (e.g., to help stay ahead of frost risks in some regions, etc.). Similarly, hybrids that are known to have high de-husk loss maybe selected for harvesting by way of the above operations, to help inhibit yield loss, and corn plants having good standability (or stalk strength) may also be selected (or prequalified). And, hybrids having germination rates that are known to be about 90% or greater, for example, may be selected (or prequalified) for harvesting by way of the above operations. However, when such hybrids are not present in the fields, the corn plants may instead be harvested again by conventional corn ear pickers, at conventional moisture contents of about 32%.

Further, corn plants that express or exhibit a likelihood for ear mold or other disease may not be selected for harvesting by way of the above operations. Instead, such corn plants may be selected for earlier harvest by way of conventional corn ear pickers (in order minimize exposure of the corn plant to the ear molds or other diseases and recover as much viable seed as possible from the corn plants).

The combine harvester 100 and the operations described herein may be implemented as part of a seed corn production program. In so doing, certain corn plants and/or fields of corn plants included in the program may be prequalified (as described above) for harvesting by the combine harvester 100 and the operations described herein (e.g., in view of the reduction in required resources (and potential cost savings) associated therewith, etc.). However, only a percentage of the prequalified corn plants and/or fields may actually be harvested by the combine harvester 100 and the operations described herein, based on the added risk involved in leaving the corn plants in the fields longer (in order to achieve the lower moisture contents required to implement the combine harvester 100). In so doing, a balance may then be derived between the cost savings associated with the operations described herein, and the added risks, whereby a predefined percentage may be implemented for the prequalified corn plants and/or fields. In other words, the seed corn production program may only harvest the predefined percentage of prequalified corn plants and/or fields by way of the combine harvester 100 and the operations described herein, and then harvest the remaining prequalified corn plants and/or fields by way of conventional corn ear pickers (at higher moisture contents and thus at soon times). In so doing, the predefined percentage may be about 10%, about 20%, about 30%, about 40%, about 50%, about 75%, about 80%, etc.

As described, the combine harvester 100 and the operations described herein may be used to produce a bulk supply of seed corn. The seed corn, then, may be used to cultivate subsequent corn plants, which product No. 2 yellow corn (e.g., for use as feed, to product ethanol, etc.). In some examples, the particular corn plants identified for harvesting for producing such seed corn are initially identified as corn plants that produce seed corn (e.g., where the corn plants are a specific hybrid of corn plants that product seed corn, etc.). And, in connection therewith, the seed corn in general may include corn kernels having particular qualities, sizes, shapes, densities, etc. (which thereby may be used to identify the corn kernels as seed corn versus No. 2 yellow corn, etc.). For instance, a bulk supply of seed corn may include corn kernels having a particular (or threshold) germination rate (e.g., a warm germination of at least about 90% and/or a cold germination of at least about 80%, etc.). A bulk supply of seed corn may also (or alternatively) include corn kernels having a particular density, such as a density sufficient for about 80,000 kernels to weight about 35 pounds. Further, a bulk supply of seed corn may (or alternatively) include particular size/shape classifications, such as either large round (AR2), medium round (AR), large flat (AF2), and/or medium flat (AF).

In some embodiments (and without limitation), the combine harvester 100 and the operations described herein may be used to harvest corn plants that have been de-tasseled (e.g., female plants, etc.). For instance, the field may be initially planted with multiple rows of corn plants, but where the corn plants in several of the rows are subsequently de-tasseled. Then, following pollination, the rows of de-tasseled corn plants (and, in some implementations, only the rows of de-tasseled corn plants) are harvested as described herein (for use in bulking up a supply of seed corn).

In some embodiments, the combine harvester 100 and operations described herein may be used as part of optimizing harvesting operations for a network of fields and associated resources. For instance, the combine harvester 100 may be included in the network as an economical harvesting option to produce seed corn in a manner that utilizes fewer resources than seed corn produced by conventional ear picking operations. In addition, the combine harvester 100 and operations described herein may enable seed corn production in areas not previously possible, due to the improved efficiency and economics associated with the combine harvester 100 (e.g., fewer resources are required to transport the seed corn, dry the seed corn, etc.). Further, by way of such the improved efficiency and economics, the combine harvester 100 and operations described herein may enable harvesting of corn together with other crops (e.g., soybeans, etc.). Moreover, the combine harvester 100 and operations described herein may be implemented to harvest a desired (or target) portion (e.g., a threshold amount, or threshold portion, or threshold percentage, etc.) of an overall harvest in the network of fields. For instance, based on the above, specific fields of corn plants (in the network of fields) (e.g., one or more of the fields in the network of fields, etc.) may be targeted (and monitored) for harvest by the combine harvester (by way of the above operations), at planting, at a start of a harvest period, earlier, later, etc., whereby in sum the harvested plants from the specific fields represent the desired (or target) portion of the overall harvest in the network of fields. In connection therewith, the desired (or target) portion may be about 5% or more, about 10% or more, about 15% or more, about 20% or more, about 25% or more, about 30% or more, about 35% or more, about 40% or more, about 50% or more, about 75% or more, percentages therebetween, etc. of the overall harvest in the network of fields.

In one example embodiment of the present disclosure, a method is provided for producing seed corn for use in growing corn plants. The method generally includes removing, by a combine harvester, cars of corn from corn plants in a field; separating the corn kernels from cobs of the cars of corn onboard the combine harvester while in the field; and collecting, by the combine harvester, a supply of the separated corn kernels for use as seed corn. In this example embodiment, in some implementations, cold germination of the collected supply of corn kernels may be at least about 75% (and, more particularly, at least about 84%), and warm germination of the collected supply of corn kernels may be at least about 75% (and, more particularly, at least about 94%).

In addition in this example embodiment, removing the cars of corn from the corn plants in the field may include removing the cars of corn from the corn plants in the field when a moisture content of corn kernels on the ears of the corn plants is about 25% or lower.

Further in this example embodiment, collecting the supply of the separated corn kernels may include collecting the supply of the separated corn kernels in a bin onboard the combine harvester. And, the example method may then additionally include transferring the collected corn kernels from the bin onboard the combine harvester to at least one dryer; drying the transferred corn kernels at the at least one dryer; and storing the dried corn kernels.

The foregoing description of the embodiments has been provided for purposes of illustration and description. It is not intended to be exhaustive or to limit the present disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

Example embodiments have been provided so that this disclosure will be thorough, and will fully convey the scope to those who are skilled in the art. Numerous specific details are set forth such as examples of specific components, assemblies, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, components, and/or groups thereof, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" and the phrase "at least one of" includes any and all combinations of one or more of the associated listed items.

Although the terms first, second, third, etc. may be used herein to describe various elements, components, seeds, members and/or sections, these elements, components, seeds, members and/or sections should not be limited by these terms. These terms may be only used to distinguish one element, component, seed, member or section from another element, component, seed, member or section. Terms such as "first," "second," and other numerical terms when used herein do not imply a sequence or order unless clearly indicated by the context. Thus, a first element, component, seed, member or section discussed below could be termed a second element, component, seed, member or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A method of using a combine harvester for producing seed corn for use in growing corn plants, the method comprising:
   identifying corn plants in a field to be harvested by the combine harvester, based on one or more characteristics of the corn plants in the field; and
   adjusting a spacing between a rotor of a threshing unit of the combine harvester and a housing of the threshing unit to generally match a diameter of cobs of the identified corn plants to be harvested; and then
   after identifying the corn plants in the field to be harvested:
      directing the combine harvester to the field including the identified corn plants;
      engaging ears of corn on the corn plants, with stalk rollers of a corn header of the combine harvester, to separate the ears of corn from stalks of the corn plants;
      transporting the separated ears of corn from the corn header into the spacing between the rotor and the housing of the threshing unit;
      directing, by the rotor, the ears of corn located within the spacing between the rotor and the housing of the threshing unit across concaves and separating grates of the housing to remove corn kernels from cobs of the ears of corn;
      moving, by a fan, the removed corn kernels across at least one sieve of a separating unit, to thereby separate the corn kernels from other material removed from the corn plants and/or ears of corn; and
      collecting, in a hopper onboard the combine harvester, the corn kernels that pass through the at least one sieve for subsequent use as seed corn.

2. The method of claim 1, further comprising:
   transporting the collected corn kernels to a processing facility and drying the corn kernels to a desired moisture content; and
   storing the dried corn kernels for use as seed corn.

3. The method of claim 2, further comprising directing the seed corn to at least one field for planting.

4. The method of claim 2, wherein the desired moisture content is about 14% or less; and
   wherein drying the corn kernels to the desired moisture content includes drying the corn kernels, by a corn ear drier, for about 11 hours or less.

5. The method of claim 1, wherein a time from which the ears of corn are separated from the stalks of the corn plants by the combine harvester to a time the kernels are stored for use as seed corn is about 25 hours or less.

6. The method of claim 1, further comprising orienting each of the ears of corn on a side portion of the ear of corn, while the ears of corn are onboard the combine harvester, and delivering the oriented ear of corn to the threshing unit, within the spacing between the rotor and the housing.

7. The method of claim 1, wherein the one or more characteristics of the corn plants are selected from the group including moisture content, corn kernel size, corn kernel shape, stalk strength, and corn plant type.

8. The method of claim 1, further comprising applying a salt spray to the identified corn plants, prior to directing the combine harvester to the field including the identified corn plants.

9. The method of claim 1, wherein the identified corn plants are included in a seed corn production program for producing seed corn from the corn plants; and wherein the method further includes prequalifying the identified corn plants to be harvested by the combine harvester, based on one or more of size and/or shape of the corn kernels of the corn plants, strength of the stalks of the corn plants, and/or types of the corn plants.

10. The method of claim 1, wherein adjusting the spacing between the rotor of the threshing unit and the housing of the threshing unit includes adjusting the spacing to between about 0.4 inches and about 1.5 inches along a length of the rotor.

11. The method of claim 10, wherein engaging the ears of corn on the corn plants with the stalk rollers of the corn header includes operating the stalk rollers of the corn header at a speed of between about 1,000 rotations per minute and about 1,200 rotations per minute.

12. The method of claim 10, wherein directing the ears of corn across the concaves and the separating grates of the housing includes operating the rotor of the threshing unit, within the housing, at a speed of between about 200 rotations per minute and about 400 rotations per minute, to push the ears of corn across the concaves and the separating grates of the housing.

13. The method of claim 10, wherein moving, by the fan, the removed corn kernels across the at least one sieve of the separating unit includes operating the fan at a speed of between about 700 rotations per minute and about 900 rotations per minute to direct air over the at least one sieve to move the corn kernels across the at least one sieve.

14. A method of using a combine harvester for producing seed corn for use in growing corn plants, the method comprising:

identifying corn plants in a field to be harvested by the combine harvester, based on one or more characteristics of the corn plants in the field; and adjusting a spacing between a rotor of a threshing unit of the combine harvester and a housing of the threshing unit to generally match a diameter of cobs of ears of corn of the identified corn plants to be harvested; and then after identifying the corn plants in the field to be harvested:

separating, by a corn header of the combine harvester, the ears of corn from stalks of the identified corn plants;

transporting the separated ears of corn from the corn header into the spacing between the rotor and the housing of the threshing unit;

directing, by the rotor, the ears of corn located within the spacing between the rotor and the housing of the threshing unit across concaves and separating grates of the housing to remove corn kernels from the cobs of the ears of corn;

directing the removed corn kernels across at least one sieve of a separating unit of the combine harvester, to thereby separate the corn kernels from other material removed from the corn plants and/or ears of corn; and collecting, in a hopper onboard the combine harvester, the corn kernels that pass through the at least one sieve for subsequent use as seed corn to grow one or more corn plants.

15. The method of claim 14, wherein the one or more characteristics of the corn plants are selected from the group including moisture content, corn kernel size, corn kernel shape, stalk strength, and corn plant type; and wherein identifying the corn plants in the field to be harvested by the combine harvester includes prequalifying the corn plants to be harvested by the combine harvester based on the identified corn plants including the one or more characteristics.

16. The method of claim 15, further comprising applying a salt spray to the identified corn plants, prior to separating the ears of corn from stalks of the identified corn plants.

17. The method of claim 14, further comprising:

transporting the collected corn kernels to a processing facility and drying the corn kernels to a moisture content of about 14% or less; and storing the dried corn kernels for use as the seed corn.

18. The method of claim 17, further comprising directing the dried corn kernels to at least one field for planting.

19. The method of claim 17, wherein drying the corn kernels to the moisture content of about 14% or less includes drying the corn kernels, by a corn ear drier, for about 11 hours or less; and wherein a time from which the ears of corn are separated from the stalks of the identified corn plants by the combine harvester to a time the kernels are stored for use as seed corn is about 25 hours or less.

20. The method of claim 14, wherein adjusting the spacing between the rotor of the threshing unit and the housing of the threshing unit includes adjusting the spacing to between about 0.4 inches and about 1.5 inches along a length of the rotor; and wherein directing the ears of corn across the concaves and the separating grates of the housing includes operating the rotor of the threshing unit, within the housing, at a speed of between about 200 rotations per minute and about 400 rotations per minute, to push the ears of corn across the concaves and the separating grates of the housing.

21. A method for producing seed corn for use in growing corn plants, the method comprising:

identifying corn plants in a field to be harvested by a combine harvester, based on one or more characteristics of the corn plants;

adjusting a spacing between a rotor of a threshing unit of the combine harvester and a housing of the threshing unit to generally match a diameter of cobs of ears of corn of the identified corn plants to be harvested; and applying a salt spray to the identified corn plants; and then separating, by a corn header of the combine harvester, the ears of corn from stalks of the identified corn plants;

transporting the separated ears of corn from the corn header into the spacing between the rotor and the housing of the threshing unit;

directing, by the rotor, the ears of corn located within the spacing between the rotor and the housing of the threshing unit across concaves and separating grates of the housing to remove corn kernels from the cobs of the ears of corn;

directing the removed corn kernels across at least one sieve of a separating unit of the combine harvester, to thereby separate the corn kernels from other material removed from the corn plants and/or ears of corn; and collecting, in a hopper onboard the combine harvester, the corn kernels that pass through the at least one sieve for subsequent use as seed corn to grow one or more corn plants.

\* \* \* \* \*